(12) United States Patent
Heuer

(10) Patent No.: US 7,019,174 B2
(45) Date of Patent: Mar. 28, 2006

(54) PREPARATION OF COLOURLESS DIBENZYLAMINE

(75) Inventor: Lutz Heuer, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 152 days.

(21) Appl. No.: 10/602,929

(22) Filed: Jun. 24, 2003

(65) Prior Publication Data
US 2004/0026226 A1 Feb. 12, 2004

(30) Foreign Application Priority Data
Jun. 26, 2002 (DE) ................. 102 28 594

(51) Int. Cl.
*C07C 209/84* (2006.01)
(52) U.S. Cl. ................................ 564/437
(58) Field of Classification Search ......... 564/437
See application file for complete search history.

(56) References Cited

U.S. PATENT DOCUMENTS

| | | | | |
|---|---|---|---|---|
| 4,709,009 A | * | 11/1987 | Fujiwara et al. | 528/481 |
| 5,107,024 A | * | 4/1992 | Kool et al. | 564/433 |
| 5,321,159 A | * | 6/1994 | Lai et al. | 564/437 |
| 5,874,619 A | | 2/1999 | Wiggins et al. | 564/437 |

FOREIGN PATENT DOCUMENTS

| | | |
|---|---|---|
| EP | 644 177 | 7/1997 |
| GB | 1 351 050 | 4/1974 |

OTHER PUBLICATIONS

Ullmann, Benzylamine; Itsuno S, Koizumi T, Okumura C, Ito K, Synthesis, (2), p. 150-152, (month unavailable) 1995, "Synthesis of Primary Amines Using Potassium 1, 1,3,3-Tetramethyldisilazide as Aminating Agent of Alkyl Halides" Department of Materials Science, Toyohashi University of Technology, Toyohashi 441, Japan.

Patent Abstracts of Japan Bd. 0161, Nr. 14 (C-0921), Mar. 23, 1992 & JP 3 287566 A (Mitsui Petrochem Ind Ltd), Dec. 18, 1991 "Zusammenfassung".

Database WPI Section Ch, Week 198049 Derwent Publications Ltd., London, GB; An 1980-87955C XP002290915 & SU 729 191 A (Rostovtseva E V) Apr. 28, 1980 "Zusammenfassung".

* cited by examiner

*Primary Examiner*—Brian J. Davis
(74) *Attorney, Agent, or Firm*—Jennifer R. Seng

(57) ABSTRACT

The invention relates to a process for preparing colourless dibenzylamine by adding ammonium chlorides or amines to the industrially obtained dibenzylamine and subsequent distillation.

11 Claims, No Drawings

PREPARATION OF COLOURLESS DIBENZYLAMINE

BACKGROUND OF THE INVENTION

1. Field of the Invention

The invention relates to a novel process for preparing colourless dibenzylamine by adding ammonium chlorides and/or amines to the industrially obtained dibenzylamine and subsequent distillation.

2. Brief Description of the Prior Art

Processes for preparing dibenzylamine in technical quality are known. Dibenzylamine may be industrially prepared from benzonitrile or benzamide by catalytic hydrogenation. Dibenzylamine may also be industrially prepared from benzonitrile or benzamide or from benzylamine or ammonia and benzaldehyde by reductive amination (EP-A-644 177). Dibenzylamine may also be obtained as a by-product from the reaction of benzyl chloride with ammonia to give benzylamine (Ullmann, Benzylamine; Itsuno S, Koizumi T, Okumura C, Ito K, Synthesis, (2), p. 150–152, 1995). These processes generally have in common the use of the reactant in a reaction mixture admixed with solvent or diluent.

To obtain the desired product, the by-products, the solvent and other secondary components usually have to be distillatively removed. However, the dibenzylamine which is obtained in such a way is coloured. In Hazen colour number of more than 100, dibenzylamine can easily be prepared without problems by the existing processes. However, when the preparation of colourless dibenzylamine is sought, i.e. dibenzylamine having a colour number of less than 100, repeated distillation is necessary. Also, the dibenzylamine prepared by the existing processes has a low stability and decomposes easily with discoloration.

As would be realised, discoloration in the use dibenzylamine, for example, to prepare stabilizers for plastics is undesirable.

SUMMARY OF THE INVENTION

The invention is based on the object of providing a process for preparing colourless dibenzylamine and thus avoiding the repeated distillation. The dibenzylamine obtained should have a high stability.

In accordance with the foregoing, the present invention encompasses a process for preparing colourless dibenzylamine having a colour number of less than 100 Hazen, which is characterized in that an additive from the group of ammonium chlorides and/or amines is added to the dibenzylamine to be purified and the mixture is then distilled. The colourless dibenzylamine prepared in this way has a high stability.

DETAILED DESCRIPTION OF THE INVENTION

The invention is described more fully hereunder with particular reference to its preferred embodiments.

Ammonium chlorides for the process according to the invention correspond to the following formula:

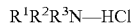

where $R^1$, $R^2$ and $R^3$ are each independently H or an organic radical.

The organic radical is a $C_1$-$C_6$-aliphatic or benzyl radical. Preference is given to benzyl radicals or H.

Among the group of ammonium chlorides represented by the above formula, very particular preference is given to ammonium chloride ($NH_4Cl$) or a mixture of benzyl-dibenzylamine hydrochlorides. Examples include ammonium chlorides such as hydrochlorides, ammonium chloride ($NH_4Cl$), or its related compounds, or aqueous or anhydrous hydrochloric acid and also benzyl chloride. Preference is given to a mixture of benzyl-/dibenzylamine hydrochlorides. Very particular preference is given to ammonium chloride ($NH_4Cl$).

The amines useful herein are those whose volatility is low so that they remain almost entirely in the residue of the distillation. Examples of the amines for the process according to the invention include high-boiling amines such as tetraethylenepentamine (TEPA) or distillation residues of tetraethylenepentamine, hexaethyleneheptamine (HEHA) or distillation residues of hexaethyleneheptamine, and pentaethylenehexamine (PEHA) or distillation residues of pentaethylenehexamine, their mixtures or mixtures with higher- or lower-boiling analogues.

For the purposes of the present invention, "high-boiling amines" are those amines which have a higher boiling point than dibenzylamine under the relevant conditions.

The ammonium chlorides and amines specified are known per se with regard to their chemical composition and obtainable as commercial products. Preference is given to using pentaethylenehexamine (PEHA) and distillation residues of tetraethylenepentamine (TEPA), very particular preference to pentaethylenehexamine (PEHA).

The amines also include polyamines which consist of a saturated hydrocarbon chain having terminal amine functions, interrupted by a varying number of secondary and/or tertiary and/or quaternary amino functions.

Preference is given to using polyamines in the process according to the invention which are selected from the group of reaction products of dichloroethane with ammonia and/or other amines from the polymerization of ethyleneimine (aziridine) or selected from the group of reaction products of ethylene oxide with ammonia or amines. These products are generally water-soluble/water-miscible liquids or solid hydrates.

Very particular preference is given to polyamines in which the polyamine corresponds to one of the following formulae (I) or (II):

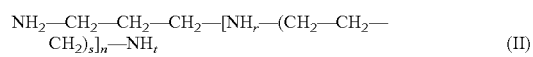

where "n" is 0 or an integer from 0 to 300,
p, q, s and t are each independently 1 and/or 2, and
r is 0 or 1, so that nitrogen is in each case triply, occasionally quadruply (ammonium salt) bonded.

These amines may be present as a free amine or as a salt, preferably as a chloride. They may also be crosslinked or branched by further reagents, for example by subsequent reactions with dichloroethane, ethyleneimine or acrylonitrile, optionally with subsequent reduction.

According to the invention, compounds from the group of ammonium chlorides or amines may be used as additives.

The additive is added to the dibenzylamine to be purified in a concentration of 0.01 to 15% by weight, preferably in a concentration of 0.1 to 3% by weight, based on dibenzylamine.

The distillation of the dibenzylamine to be purified is preferably controlled in such a way that a bottom temperature of 120 to 220° C., preferably of 160 to 200° C., is obtained. The pressure is preferably set in such a way that the mixture boils under the temperature conditions. Typically, the pressure is set at 100 to 0.1 mbar and preferably at 50 to 5 mbar. After coloured first running, the product obtained is pure dibenzylamine having a colour number of <100 Hazen.

This process reliably gives a colour number of less than 100 Hazen. In general, products having colour numbers <30 Hazen (colourless), and often colour numbers <10 Hazen, are observed.

For the purposes of the present invention, the colour number is a characteristic value determined under standard conditions for the colour of transparent substances which is determined by visual comparison. This can be obtained by comparison with standard colour tables, for example according to DIN EN 1557 (March 1997) or by comparison with standardized solutions.

In order to stabilize the pure dibenzylamine, it is stored under nitrogen. In addition to nitrogen, addition of hydrazine (aqueous or anhydrous) or hydroxylamine (aqueous or anhydrous) allows the storage time to be distinctly increased with unchanged or only slightly changed colour number. The additives hydrazine and hydroxylamine are used individually or as a mixture in concentrations of 0.01 to 10.0% by weight, based on the pure dibenzylamine.

The process according to the invention is illustrated by the example which follows; percentages are percentages by weight.

EXAMPLE 591 g of a sidestream from the preparation of benzylamine which comprises 0.1% of water, 18% of benzylamine, 0.5% of benzyl alcohol, 77.9% of dibenzylamine and also 0.7% of benzalbenzylamine and approx. 3% of other components is admixed with 2.2 g of ammonium chloride and 7.5 g of pentaethylenehexamine and heated to 200° C.

After fractional distillation, 423 g (92% of theory) of dibenzylamine having a colour number of 11 Hazen and a purity of 99.74% are obtained. The colour number was determined by an instrument from Dr. Lange in Düsseldorf in accordance with DIN EN 1557.

The product is admixed with hydroxylamine (0.04%) under nitrogen and is storage-stable. Storage at 60° C. for 28 days changes the colour number to 30 Hazen. Without hydroxylamine as stabilizer, the colour number after 28 days changes to 90 Hazen.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for preparing colourless dibenzylamine having a colour number of, less than 100 Hazen, comprising adding an additive selected from the group of ammonium chlorides and/or amines to the dibenzylamine to be purified and distilling the resulting mixture.

2. Process according to claim 1, characterized in that the ammonium chloride corresponds to the following formula:

$$R^1R^2R^3N\text{---}HCl,$$

where
$R^1$, $R^2$ and $R^3$ are each independently H or an organic radical,
which is a C1–C6-aliphatic or benzyl radical.

3. Process according to claim 1, characterized in that the ammonium chloride is benzyl chloride, a hydrochloride, ammonium chloride or aqueous or anhydrous hydrochloric acid, or a mixture of benzyl-/dibenzylamine hydrochlorides.

4. Process according to claim 1, characterized in that the amine has a higher boiling point than dibenzylamine.

5. Process according to claim 1, characterized In that the amine is tetraethylenepentamine or distillation residues of tetraethylenepentamine, hexaethyleneheptamine or distillation residues of hexaethyleneheptamine, pentaethylenehexamine or distillation residues of pentaethylenehexamine.

6. Process according to claim 1, characterized in that the amine is a polyamine from the group of reaction products of dichloroethane with ammonia and/or amines or from the group of reaction products of ethylene oxide with ammonia or amines.

7. Process according to claim 1, characterized in that the additive is added to the dibenzylamine to be purified in a concentration of 0.01 to 15% by weight based on dibenzylamine.

8. Process according to claim 1, characterized in that the distillation of the dibenzylamine to be purified has a bottom temperature of 120 to 220° C., and that the pressure is set at a level effective to boil the mixture under the temperature conditions.

9. Process according to claim 1, characterized in that the resulting pure dibenzylamine is stabilized under nitrogen.

10. Process according to claim 9, characterized in that the pure dibenzylamine is stabilized by adding aqueous or anhydrous hydrazine or aqueous or anhydrous hydroxylamine.

11. Process according to claim 10, characterized in that the hydrazine or the hydroxylamine is added to the pure, light-coloured dibenzylamine individually or as a mixture in concentrations of 0.01 to 10% by weight.

* * * * *